United States Patent
Bosma et al.

(10) Patent No.: US 8,133,253 B2
(45) Date of Patent: Mar. 13, 2012

(54) VASCULAR FILTER WITH SLEEVE

(75) Inventors: Gjalt Bosma, Opeinde (NL); Yvonne L. Hoogeveen, Groningen (NL); Michiel Koorn, Boraxstraat (NL); Rudolf T. Mulder, Groningen (NL)

(73) Assignee: Cordis Corporation, Miami Lakes, FL (US)

( * ) Notice: Subject to any disclaimer, the term of this patent is extended or adjusted under 35 U.S.C. 154(b) by 502 days.

(21) Appl. No.: 12/082,995

(22) Filed: Apr. 16, 2008

(65) Prior Publication Data

US 2009/0069839 A1 Mar. 12, 2009

Related U.S. Application Data

(62) Division of application No. 10/923,453, filed on Aug. 20, 2004, now abandoned.

(51) Int. Cl.
*A61M 29/00* (2006.01)
(52) U.S. Cl. .................................................. 606/200
(58) Field of Classification Search .............. 606/200, 606/110, 113, 114, 198; 623/1.11, 1.13
See application file for complete search history.

(56) References Cited

U.S. PATENT DOCUMENTS

| | | | |
|---|---|---|---|
| 3,799,590 A | 3/1974 | Messa | |
| 4,793,348 A | 12/1988 | Palmaz | |
| 4,990,156 A | 2/1991 | Lefebvre | |
| 5,108,418 A | 4/1992 | Lefebvre | |
| 5,242,462 A | 9/1993 | El-Nounou et al. | |
| 5,350,398 A * | 9/1994 | Pavcnik et al. | 606/200 |
| 5,413,586 A | 5/1995 | Dibie et al. | |
| 5,531,788 A | 7/1996 | Dibie et al. | |
| 6,099,549 A | 8/2000 | Bosma et al. | |
| 6,241,746 B1 | 6/2001 | Bosma et al. | |
| 6,267,777 B1 | 7/2001 | Bosma et al. | |
| 6,443,972 B1 * | 9/2002 | Bosma et al. | 606/200 |
| 6,989,021 B2 * | 1/2006 | Bosma et al. | 606/200 |
| 7,217,255 B2 * | 5/2007 | Boyle et al. | 604/104 |
| 2002/0028857 A1 | 3/2002 | Holy | |
| 2003/0023265 A1 * | 1/2003 | Forber | 606/200 |
| 2003/0139764 A1 * | 7/2003 | Levinson et al. | 606/200 |
| 2003/0204168 A1 * | 10/2003 | Bosma et al. | 604/103.02 |
| 2004/0087999 A1 | 5/2004 | Bosma et al. | |
| 2004/0199201 A1 * | 10/2004 | Kellett et al. | 606/200 |
| 2004/0225322 A1 * | 11/2004 | Garrison et al. | 606/200 |
| 2005/0234501 A1 | 10/2005 | Barone | |

* cited by examiner

*Primary Examiner* — Amy Lang

(57) ABSTRACT

A covered vascular filter can be placed in a blood vessel, for the purpose of intercepting thrombus. The filter may be introduced to a desired site for medical treatment through a catheter which defines a lumen or passage and a distal port or opening. The filter tends to resiliently expand from a compressed shape when it is inside the catheter lumen, to an expanded shape when the filter is pushed from the catheter lumen. A cover or sleeve over those portions of the filter that would otherwise contact the vessel wall tends to reduce pressure on the vessel wall. The sleeve also tends to resist growth of the vessel wall among the elements of the filter, called endothelialization. In other words, the sleeve resists incorporation of the filter elements into the vessel wall, enabling the filter to be retrievable for a longer time. The various features of the present invention may be used singly or in any combination, as desired in a particular vascular filter.

10 Claims, 5 Drawing Sheets

VASCULAR FILTER WITH SLEEVE

CROSS-REFERENCE TO RELATED APPLICATIONS(S)

This patent application is a divisional of U.S. patent application Ser. No. 10/923,453 filed on Aug. 20, 2004 now abandoned entitled "Vascular Filter With Sleeve".

BACKGROUND AND SUMMARY OF THE INVENTION

1. Technical Background

The present invention relates to a vascular filter with a sleeve covering, which can be temporarily or permanently placed inside a blood vessel for the purpose of intercepting thrombus.

2. Discussion

Some basic types of vascular filters are generally known, wherein a single filter element, mesh or member extends across the direction of flow inside a blood vessel. Several features may be desirable for vascular filters, including non-surgical or "percutaneous" delivery of the filter to a desired site, and expansion from a preferably small initial size to an expanded working size that matches the vascular anatomy at the desired site. Also, a vascular filter should preferably capture a sufficient percentage of thrombus, while allowing blood to flow freely through the filter.

Another desirable feature is a capability to remain reliably in the desired position in a patient's anatomy, referred to as "position retention." One simple attempt at position retention is to wedge a vascular filter against the blood vessel wall by sizing it with a dimension slightly larger than the inside diameter of the blood vessel. In addition, a vascular filter should preferably have a design whereby the filter is self-centering and stable in the vessel, such that the filter has a tendency not to "tilt", which might result in less effective capturing of thrombus. Some vascular filters may be used in the vena cava, and may be described in such event as a "vena cava filter."

A vascular filter may be delivered through a catheter in a compressed shape, the filter tending to resiliently expand within a blood vessel and to retain the desired position and orientation. The vascular filter tends to trap thrombus or particles, and resist their movement further downstream. The filter includes, in a position of use, an outer shape corresponding to the internal diameter of the blood vessel, and one or more filter elements extending across the vessel.

In the temporal sense, there are three type of filters: (i) permanent filters, intended for permanent implantation; (ii) temporary filters, intended for removal within a time period; and (iii) retrievable filters, in which the physician has the option to implant the filter permanently or to remove the filter after some time. In the case of a retrievable filter, the filter may be designed so that the physician can choose whether to retrieve the filter at a later date, after the filter has been in place for a while. This way, the physician can evaluate the performance of the filter and the patient's condition, before deciding whether to retrieve the filter or not.

To help in successful retrieval, one factor is to avoid "endothelialization" or in-growth of the vessel wall and tissue around the structural members of the filter. In other words, endothelialization is the healing of the vessel inner surface by endothelial cells. It is desirable to preserve these endothelial cells when removing a retrievable vascular filter, and the improved designs of the present invention tend to minimize any impact during retrieval.

On a filter, it may also be desirable to provide releasable temporary position stabilizers, to resist tilting and to enhance position retention. Some vascular filters provide anchors or small barbs for improving position retention, which extend in radial directions outward from the ribs. Some filters may have barbs cut out from a central section of the filter. The barbs tend to gently hold the filter in place inside the vessel.

A vascular filter along the lines of the present invention may provide several advantages, including effectively capturing thrombus while allowing blood flow, resisting endothelialization of the filter, and distributing expansive pressures of the filter to a greater area of the vessel wall. In other words, there is less stress on the vessel wall, and the sleeve enables a physician to have a longer time before choosing whether to retrieve a retrievable filter.

A vascular filter may have an initial compressed shape, in which the filter may have essentially a tubular shape, and may be contained in a lumen or passage defined by a catheter.

After a distal tip of the catheter reaches a desired site for treatment, a wire mandrel or other deployment device may be used to push the filter out of the catheter. And when the filter is released from the catheter, it tends to resiliently expand from the initial compressed shape to an expanded shape. When a vascular filter is retrieved from a blood vessel, the entire filter is resiliently compressed to a relatively small diameter, for extraction through a catheter.

A filter according to the present invention has a flexible tubular covering on at least a portion of the filter. As a result, the filter exerts less expansive pressure on the vessel wall, and tends to resist incorporation into the vessel wall for a longer period of time.

The term "filter" will be used interchangeably, to refer to either (i) a combination device including a resilient scaffold structure with a sleeve covering, or (ii) only the scaffold component, or (iii) those portion(s) of the scaffold which operate to capture thrombus.

The term "tubular" is used in its broadest sense, to encompass any structure arranged a radial distance around a longitudinal axis. Accordingly, "tubular" includes any structure that (i) is cylindrical or not, such as for example an elliptical or polygonal cross-section, or any other regular or irregular cross-section; (ii) has a different or changing cross-section along its length; (iii) is arranged around a straight, curving, bent or discontinuous longitudinal axis; (iv) has an imperforate surface, or a periodic or other perforate, irregular or gapped surface or cross-section; (v) is spaced uniformly or irregularly, including being spaced varying radial distances from the longitudinal axis; (vi) has any desired combination of length or cross-sectional size.

A vascular filter may include a first and second filter section, arranged on either side of a body section. The body section and the filter sections thus enclose a space. Due to the elongated shape of the vascular filter, and the arranging of the first and second filter sections on either side of the body member, the present filter may have an enhanced filtering effect. In other words, two opportunities have been created for intercepting thrombus moving inside the blood vessel.

A central tubular section tends to resiliently exert slight outward pressure along a large section of contact area on the blood vessel wall. The sleeve distributes this outward pressure to a greater area. Accordingly, the filter tends to exert some small amount of pressure on the internal wall of the blood vessel, and tends to hold itself in place. The vascular filter will consequently tend not to shift position.

In addition, because of this elongated shape the vascular filter tends to center itself within the lumen, and not to rotate transversely or tilt over.

In an example, a vascular filter may be formed out of one single piece, which provides advantages including simplicity.

When viewed along the longitudinal axis of the filter, the filter sections may have the shape of a regular polygon, and thus may provide several smaller filtering "cells". The purpose of these filtering cells is to intercept thrombus moving inside the blood vessel, and the smaller filtering cells tend to capture more thrombus. All the cells may be of the same size, to provide a uniform filtering effect.

The filter sections, as arranged according to an embodiment described above on either side of the tubular body section, may be identical in shape, thereby enhancing the simplicity of the vascular filter according to the present invention.

The sleeve of the present invention may be made of any suitable material, and may be affixed to the filter by friction alone, or with fasteners or adhesives of any suitable type. The sleeve may be foil, and/or may be elastic or inelastic. In addition, the sleeve may be biodegradable.

It is of course possible to build various vascular filters according to the present invention, by various techniques and of various materials to obtain the desired features. It should be noted that the present invention also relates to methods for manufacturing vascular filters, and for using vascular filters for medical treatment of a patient.

These and various other objects, advantages and features of the invention will become apparent from the following description and claims, when considered in conjunction with the appended drawings. The invention will be explained in greater detail below with reference to the attached drawings of a number of examples of embodiments of the present invention.

DETAILED DESCRIPTION OF THE PREFERRED EMBODIMENTS

The following description of the preferred embodiments of the present invention is merely illustrative in nature, and as such it does not limit in any way the present invention, its application, or uses. Numerous modifications may be made by those skilled in the art without departing from the true spirit and scope of the invention.

The drawings depict a vascular filter medical device 10 along the lines of the present invention. The drawings depict an example vascular filter medical device 10, which includes a filter structure 12 and a sleeve 14. Sleeve 14 is affixed to filter structure 12 in any suitable manner, including adhesives, stitching, or simply weaving sleeve 14 among the members of filter structure 12.

Figure 1:
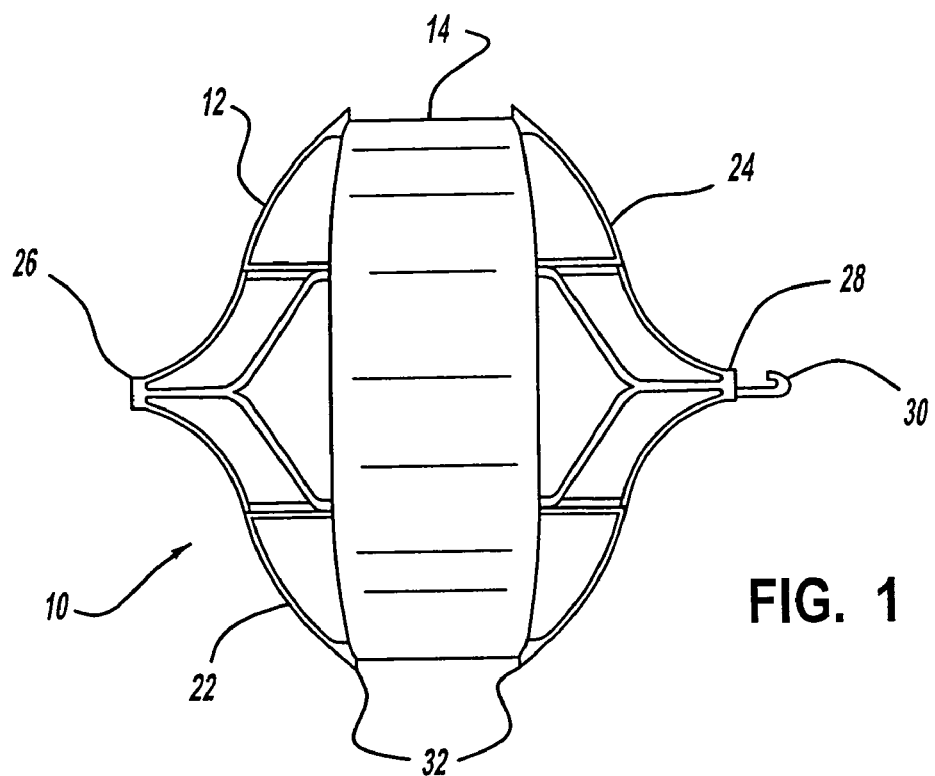
FIG. 1 shows a side elevation view of a vascular filter with a sleeve covering, arranged according to the principles of the present invention.
Figure 2:
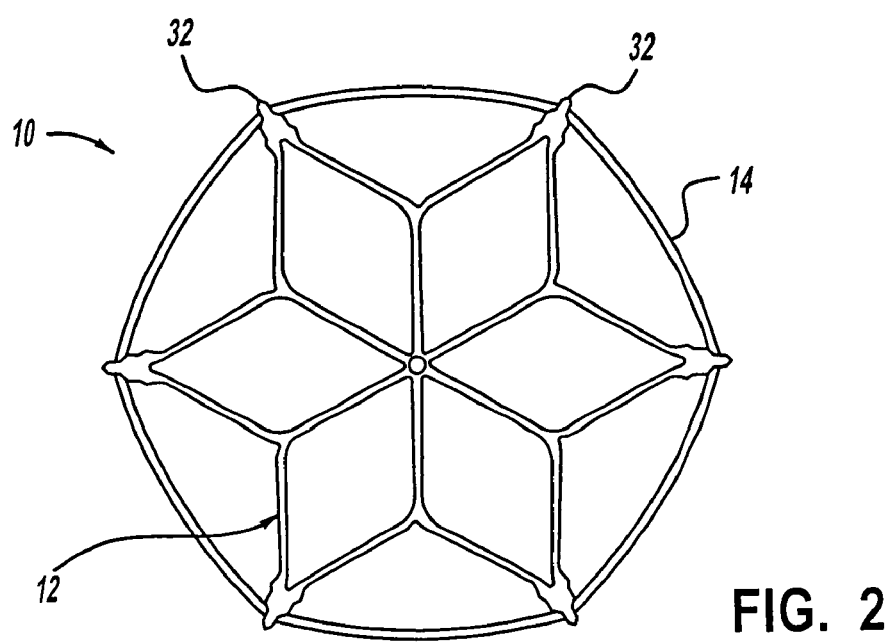
FIG. 2 illustrates an end elevation view of the vascular filter and sleeve covering of FIG. 1.
Figure 4:
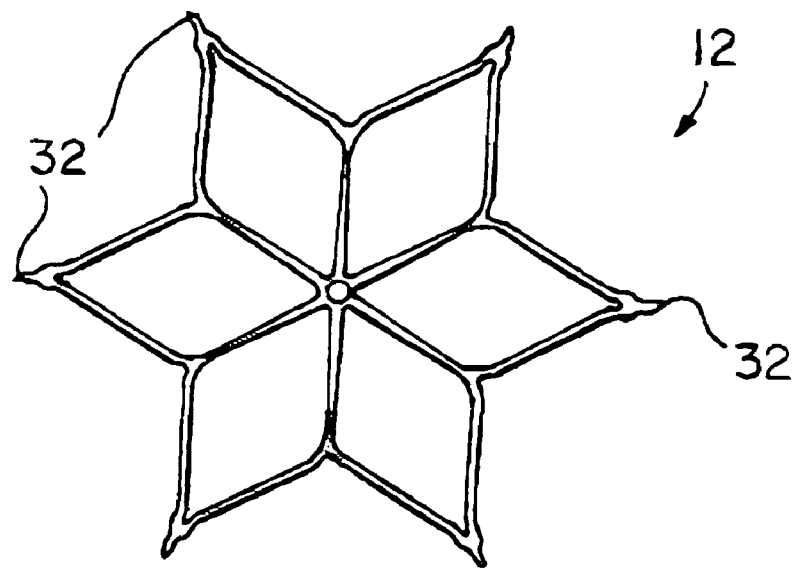
FIG. 4 shows an end elevation view of a vascular filter.
Figure 9:
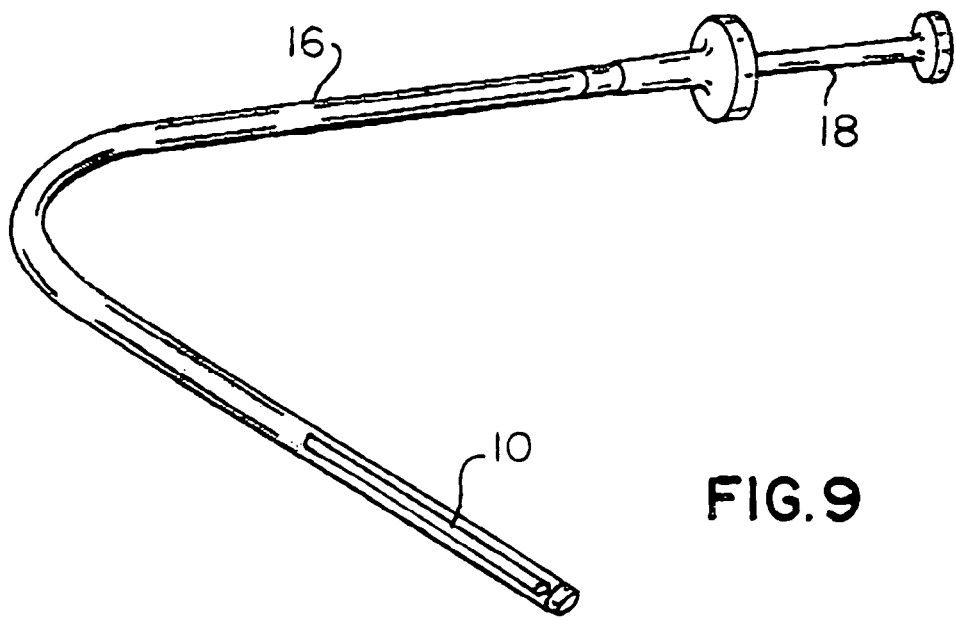
FIG. 9 is a perspective view of a catheter-based medical device delivery system.
Figure 10:
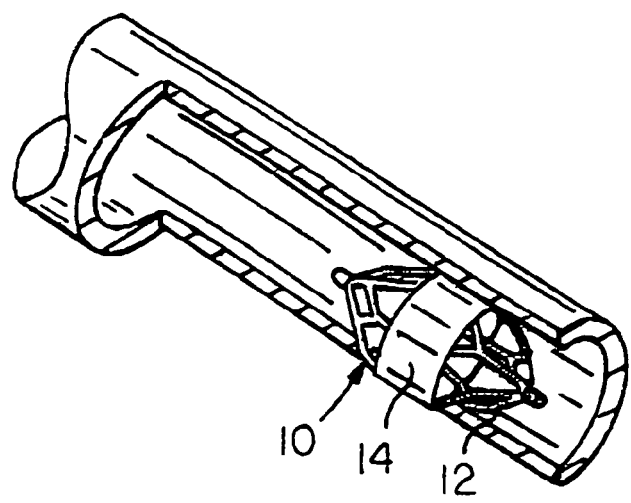
FIG. 10 is a partial cutaway view of a vascular filter inside a blood vessel.

Medical device 10 has an expanded shape, shown in FIGS. 1 and 2, and an initial compressed shape, shown in FIG. 9. If medical device 10 is delivered with a catheter 16, and a pushing wire or mandrel 18, medical device 10 will have the initial compressed shape when it is within a passage or lumen of the catheter 16. In this configuration, the filter 12 may have a tubular shape, and a pattern of filter members may be affixed together or be made of a single piece of material with a patterned series of cuts.

In any event, filter 12 tends to resiliently expand from the initial compressed shape to the expanded shape. Sleeve 14 tends to unfold as filter 12 expands resiliently from the initial compressed shape to the expanded shape. Once the filter 12 is in the expanded shape, it tends to resiliently maintain that expanded shape, when deployed at a desired site for treatment within a body passage or vessel.

The terms "filter" or "vascular filter" or "filtering" may be used in a broad or interchangeable fashion to refer generally to the entire medical device 10, filter structure 12, the first and second filtering section 22 and 24, the filtering effect on body fluids or particulates, or the results of such a filtering effect, or any other relevant aspect of the present invention.

Structurally, filter 12 has a central section 20, flanked by a first and second filtering section 22 and 24, which are flanked by a first and second end 26 and 28. The particular example depicted in the drawings is made from a single piece of tubular material, with a patterned series of cuts, which is treated to resiliently expand and form the filtering mesh structure. The filter structure could of course also be formed of multiple members which are affixed together.

Sleeve 14 may have a generally tubular or annular structure, such that whatever configuration or shape may be selected for the sleeve, it encircles all or a portion of filter 12 around its longitudinal axis. Sleeve 14 may be made of a foil, film or a metal or polymer material. Also, sleeve 14 may be made of elastic or inelastic material. In addition, sleeve 14 may also be made of biodegradable material.

The sleeve tends to distribute expansive pressures of the members of filter 12 to a greater portion of an inner wall of a body passage or vessel in which the medical device 10 is implanted.

While the medical device 10 is implanted within a patient, body tissues naturally tend to incorporate or endothelialize implanted objects. This process of endothelialization may take place over a predictable period of time, and when a filter or other medical device has been incorporated or endothelialized, it may be preferred to leave it in place indefinitely. Sleeve 14 may tend to extend this period of time of incorporation, allowing medical filter 10 to remain in place and provide therapeutic benefit for a longer period of time, yet continue to be retrievable.

If the medical device is intended to be a temporary or a retrievable filter, such that the filter may be removed or retrieved at a later time, the filter may be provided with features advantageous to such possible retrieval. For example, filter 12 may have on one or both ends a hook or loop construction, such as for example retrieval hook 30. Hook 30 may be used to extract the medical device 10 back into a catheter by means of a cooperating hook, snare or grabbing member.

In the compressed shape when the vascular filter is inside the catheter, the filter may include cuts extending in the longitudinal direction of the filter between, but not as far as, the ends of the filter. The cuts define strips of material as illustrated in the drawings. These strips expand to form the filtering first and second mesh. The specific cuts consequently also form the filter elements 22 and 24 on either side of the filter 12. The strips extend in a generally longitudinal direction.

The vascular filter 12 embodiment illustrated here may of course be used in the vena cava or any other desired site for treatment. The filter 12 preferably includes a number of ribs extending in a longitudinal direction along the internal wall of the blood vessel or body passage. These ribs together form central body section 20. Each filter section 22 and 24 form a grid shape. Liquid inside the blood vessel can pass through the vascular filter 12, but thrombus or particulates tend to be intercepted by one of the two filter sections 22 or 24.

Another advantage of this configuration is that it provides two filter elements for intercepting thrombus moving inside the blood vessel. In addition, due to the sleeve and the filter shape, the filter provides less possibility for any trauma to a vessel.

As the filter sections 22 and 24 have been arranged on either side of the central body of the filter, a longitudinally symmetrical shape has been obtained (except for hook 30). There is no difference whether the vascular filter is placed forward or backward inside the blood vessel. In other words, the proximal and distal ends of the filter are identical and symmetrical. Accordingly, a single pre-loaded catheter system may be used to deploy a filter at a desired site, from either an upstream or downstream direction.

Figure 3:
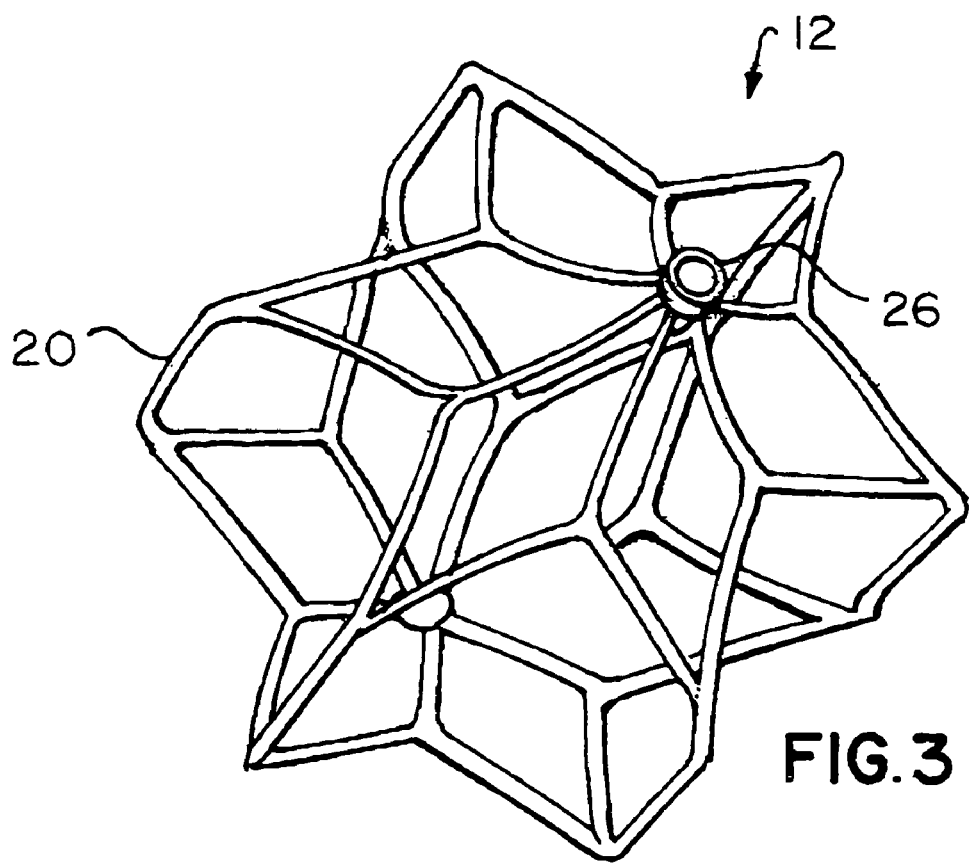
FIG. 3 shows a perspective view of a vascular filter.
Figure 6:
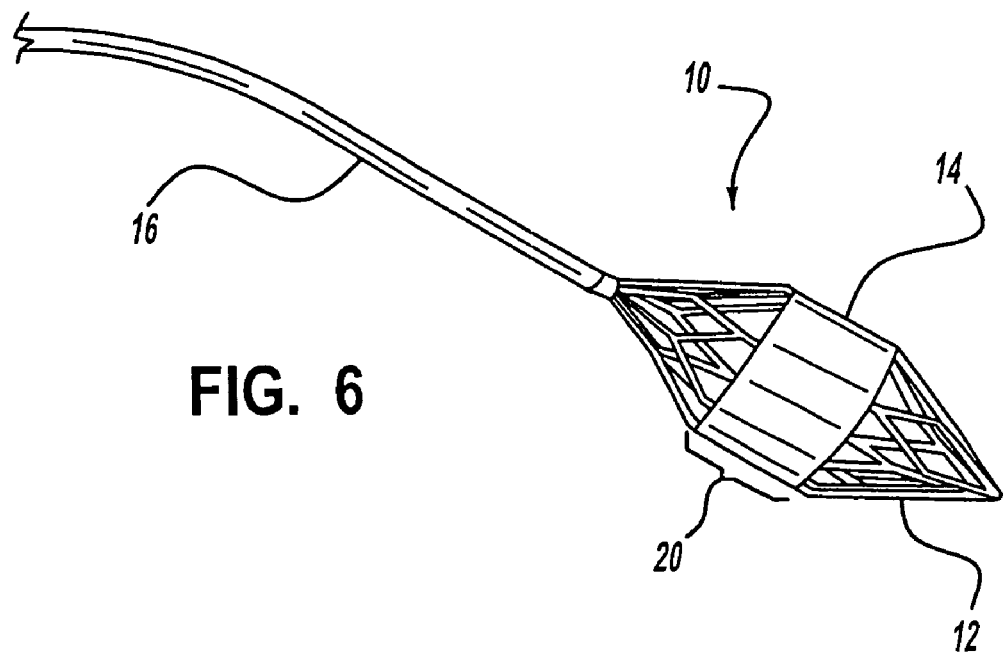
FIGS. 5 and 6 are side elevation views of vascular filters during deployment from a catheter.
Figure 5:
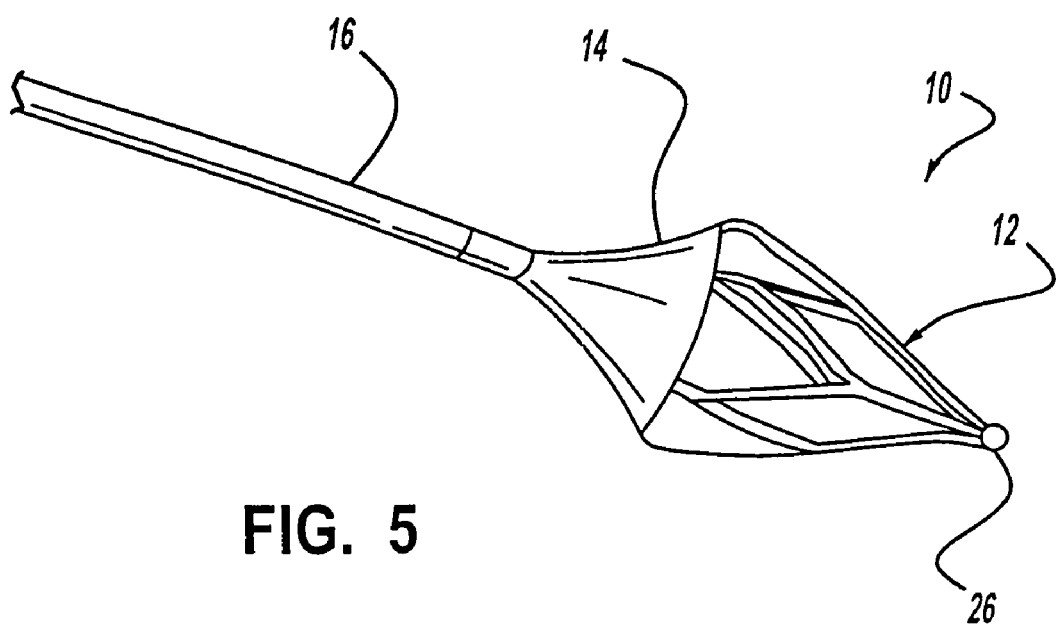
Figure 7:
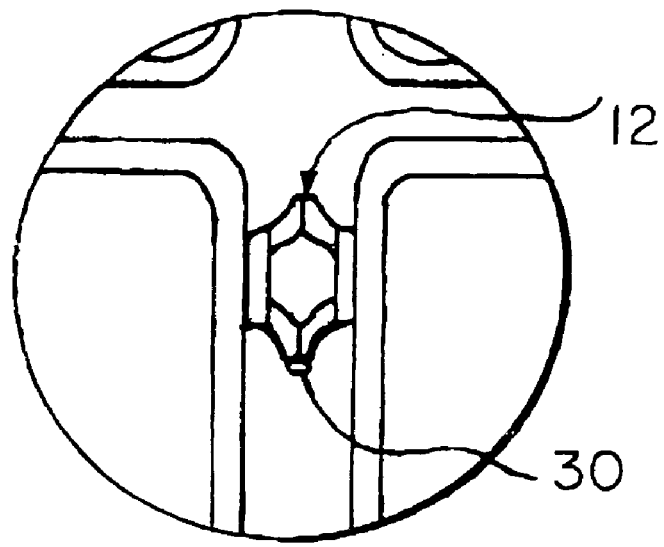
FIG. 7 is a plan view of a vascular filter inside a blood vessel.
Figure 8:
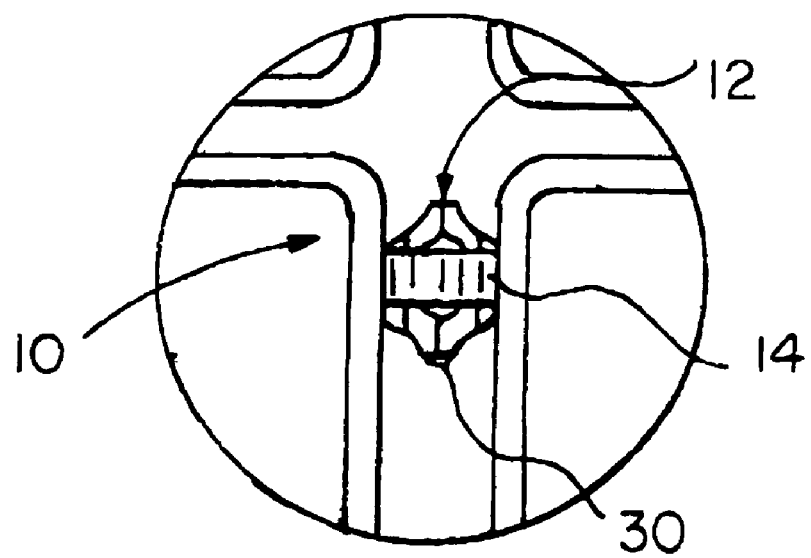
FIG. 8 is a plan view of a vascular filter with sleeve covering inside a blood vessel.

In the axial view of FIG. 3, the filter sections on either side of the ribs of the vascular filters according to the present invention described above display diamond or polygon shapes. It is also possible to provide vascular filters of which the filter sections display in axial view a star shape, or any other suitable shape, as long as they successfully intercept blood clots or thrombus. An advantage of this feature is that, after passing the first filter section 28 and the tubular section or the elongated body member, a second filter element 30 for intercepting thrombus has been provided. Also, other shapes of the filter sections in axial view are possible, which shapes will occur to those skilled in the field after reading the present description. The shapes of the filter sections in axial view need not be symmetrical, and may in principle have any suitable appearance.

As shown in the drawings, the filter 12 preferably has one or more barbs or anchors 32, located on one or more of the longitudinal ribs. The anchors 32 may be positioned at one or both ends of the longitudinal ribs, and may be directed in the proximal or distal directions. In a preferred embodiment, the sleeve 14 encircles the longitudinal ribs without being penetrated by the barbs or anchors 32. As shown, opposing sets of proximal and distal anchors 32 may be arranged to face in both longitudinal directions respectively. This opposing arrangement causes the anchors 32 to resist movement of the filter 12 in both longitudinal directions.

The filter 12 may for example be delivered to the vascular region in the general area of the heart from either a femoral artery access point in the leg, or a jugular artery access point in the neck. Because the filter shown in FIG. 2 is longitudinally symmetrical, the same filter delivery system 10 may be used for either femoral or jugular access, because the opposing sets of anchors 32 will resist downstream migration of the filter, regardless of the longitudinal orientation of the filter.

Furthermore, retraction of a vascular filter according to the present invention is mentioned above, which should not limit the scope of the claims attached. Regarding the subject of the invention, it is therefore of no consequence whether the filter is placed permanently, in a removable manner, temporarily or otherwise.

In addition to the nitinol mentioned so far, many other materials may also be used for manufacturing a vascular filter according to the present invention. By way of alternative, various metals may for instance be used, including stainless steel. In any case, the vascular filter preferably tends to resiliently assume the intended shape after having been ejected from the catheter.

Vascular filters according to the present invention may be made of any suitable material using a variety of methods. One material having the desired characteristics of strength, resilience, flexibility, biocompatibility and endurance is nitinol. Other possible materials include stainless steel and any other material having the desired properties.

Likewise, the manufacturing methods for the filter of the present invention may include providing a tube, and then cutting a pattern into the tube to enable expansion into the desired shape. Various other methods are of course possible, including forming the filter of discrete members and joining or connecting the members, or chemically etching a substrate. The manufacturing methods may include an inflatable or expandable mold, heating or cooling, welding, etc.

In FIG. 9, a medical device 10 is loaded into a catheter 16 lumen which extends from a proximal end having a hub to a distal opening. At least one vascular filter 12 is preferably arranged, in a compressed state, in the distal end of the catheter. The filter 12 is then pushed out the catheter distal opening by a flexible pushing wire 18.

In an alternative embodiment, it is also possible that the filter 12 may be inserted at the proximal end of the catheter 16, and then pushed along the entire length of the catheter 16 by the pushing wire 18, after the catheter distal end 20 has been advanced to the desired position.

In any event, when the vascular filter 12 is ejected by the pushing wire 18 out from the distal tip of the catheter 16 into the blood vessel, the vascular filter 12 will tend to resiliently expand after being released from the catheter 16. The material and design of the filter 12 results in resilient expansive forces that tend to cause the vascular filter 12 to take the illustrated shape.

It should be understood that an unlimited number of configurations for the present invention could be realized. The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

What is claimed is:

1. An implantable medical device for therapeutic treatment of a patient, comprising:
   a filter having first and second tubular ends, and a central expandable portion extending between the ends to define a longitudinal axis; the central portion tending to resiliently expand in radially outward directions from a compressed initial shape to an expanded deployed shape; the filter having proximal and distal ends that are identical and symmetrical;
   wherein the filter defines first and second filtering elements in the expanded shape, the first and second filtering elements each being near the first and second tubular ends, respectively;
   the filter having a central section formed from a plurality of longitudinally oriented rectilinear ribs arranged parallel to the longitudinal axis, the ribs being connected between the first and second filtering elements to enclose a space and form a structure having a longitudinally symmetrical shape, each rib having first and second ends; the ribs configured to expand in radially outward directions when the filter expands from the compressed shape to the expanded shape, thereby causing the first and second tubular ends to move toward each other and;

the filter having a retrieval hook affixed to the first tubular end, for optionally retrieving the filter after implantation to treat a patient;

the filter having at least one anchor for enhancing position retention, the at least one anchor attached to and extending from the first or second end of at least one of the plurality of ribs; and a flexible sleeve encircling the plurality of ribs around the longitudinal axis without being penetrated by the at least one anchor, the flexible sleeve being configured so it only covers the central section; the sleeve defining a surface area; the sleeve configured to expand with the filter central portion to an expanded shape in which the sleeve represents a cylindrical surface for contracting a blood vessel wall, the central section, first and second filtering elements and flexible sleeve forming the filter having a longitudinally symmetrical shape to allow bi-directional filtering.

2. The medical device of claim 1, wherein the sleeve is made of foil.

3. The vascular filter as set forth in claim 1, wherein the sleeve tends to reduce pressure imparted by the filter on a blood vessel wall.

4. The medical device of claim 1, wherein the sleeve is made of biodegradable material.

5. The medical device of claim 1, wherein the sleeve extends a time in which the medical device is endothelialized into the blood vessel wall.

6. The medical device of claim 1, wherein the sleeve is made of elastic material.

7. The medical device of claim 1, wherein the sleeve is made of inelastic material.

8. A medical system for therapeutic treatment of a patient, comprising:

a filter with a flexible sleeve, a catheter, and a pushing wire;

the filter having first and second tubular ends, and a central expandable portion extending between the ends; the central portion configured to resiliently expand in radially outward directions from a compressed initial shape to an expanded deployed shape; wherein the filter defines a first and second filtering element in the expanded shape, the first and second filtering elements each being near the first and second tubular end, respectively;

the filter having a plurality of ribs arranged in a pre-selected pattern, each rib having a first and a second end; such that the ribs expand in radially outward directions when the filter expands from the compressed shape to the expanded shape, thereby causing the first and second ends to move toward each other;

the filter having a retrieval hook affixed to the first tubular end, for optionally retrieving the filter after implantation to treat a patient;

the filter having at least one anchor for enhancing position retention, the anchor extending from the first and/or second end of at least one rib;

the flexible sleeve encircling at least a portion of the filter, around a longitudinal axis defined between the first and second ends without being penetrated by the at least one anchor and covering only the plurality of ribs; the sleeve defining a surface area; the sleeve configured to expand with the filter central portion to an expanded shape in which the sleeve represents a tubular surface for contracting a blood vessel wall;

the catheter having a proximal and distal end, and a defining a lumen extending between the proximal and distal ends;

the pushing wire being inserted within the lumen; and wherein the filter and sleeve are within the lumen of the catheter in the initial compressed shape.

9. The medical device of claim 1, wherein the filter has a plurality of anchors, and the sleeve spans a longitudinal distance between the anchors.

10. The medical device of claim 1 wherein the first and second filtering elements comprise polygon shaped filtering cells when viewed along the longitudinal.

* * * * *